(12) United States Patent
Schönhoff et al.

(10) Patent No.: US 10,197,530 B2
(45) Date of Patent: Feb. 5, 2019

(54) METHOD AND DEVICE FOR TESTING TEST OBJECTS FOR THE PRESENCE OF DAMAGE

(71) Applicant: INTRAVIS Gesellschaft fur Lieferungen und Leistungen von bildgebenden und bildverarbeitenden Anlagen und Verfahren mbH, Aachen (DE)

(72) Inventors: Klaus Schönhoff, Würselen (DE); Holger Zirnig, Ratingen (DE); Olaf Koziessa, Geilenkirchen (DE); Gerd Fuhrmann, Aachen (DE)

(73) Assignee: INTRAVIS GESELLSCHAFT FÜR LIEFERUNGEN UND LEISTUNGEN VON BILDGEBENDEN UND BILDVERARBEITENDEN ANLAGEN UND VERFAHREN MBH, Aachen (DE)

( * ) Notice: Subject to any disclaimer, the term of this patent is extended or adjusted under 35 U.S.C. 154(b) by 0 days.

(21) Appl. No.: 15/557,533

(22) PCT Filed: Oct. 21, 2016

(86) PCT No.: PCT/EP2016/075390
§ 371 (c)(1),
(2) Date: Sep. 12, 2017

(87) PCT Pub. No.: WO2017/072044
PCT Pub. Date: May 4, 2017

(65) Prior Publication Data
US 2018/0100829 A1   Apr. 12, 2018

(30) Foreign Application Priority Data
Oct. 27, 2015  (DE) .................. 10 2015 118 287

(51) Int. Cl.
*G01N 27/61*  (2006.01)
*G01N 27/92*  (2006.01)
*G01R 31/16*  (2006.01)

(52) U.S. Cl.
CPC ............. *G01N 27/61* (2013.01); *G01N 27/92* (2013.01); *G01R 31/16* (2013.01)

(58) Field of Classification Search
CPC ........... G01N 27/228; G01N 33/48785; G01N 35/1011; G01N 2035/1025; G01N 2035/1032; G01N 2035/1034
(Continued)

(56) References Cited

U.S. PATENT DOCUMENTS

| | | |
|---|---|---|
| 4,155,093 A | 5/1979 | Fotland et al. |
| 4,914,395 A | 4/1990 | Hamada |

(Continued)

FOREIGN PATENT DOCUMENTS

| | | |
|---|---|---|
| DE | 3136538 A1 | 9/1982 |
| DE | 3213100 A1 | 9/1983 |

(Continued)

OTHER PUBLICATIONS

International Search Report dated Feb. 1, 2017 for PCT/EP2016/075390 and English translation.

*Primary Examiner* — Melissa Koval
*Assistant Examiner* — Trung Nguyen
(74) *Attorney, Agent, or Firm* — Lucas & Mercanti, LLP

(57) ABSTRACT

A method and a device for testing for the presence of micro-holes or microcracks in a bottom surface of test objects includes an upper electrode arranged above a transport level and a lower electrode arranged below the transport level. The magnitude of a test voltage generated by two voltage sources connected in series is controlled at the electrodes so that the test voltage is greater than or equal to (Continued)

the breakdown voltage between the electrodes in air, and smaller than the breakdown voltage through a test object without holes or cracks. The test voltage is controlled temporally and synchronously with the movement of the test objects, so that the test voltage is only applied when one of the test objects is located between the electrodes. A hole or crack is recognized by a breakdown to the discharge path between the electrodes.

29 Claims, 4 Drawing Sheets

(58) Field of Classification Search
USPC ... 324/677–688, 600, 755.11, 756.04, 76.11, 324/76.32, 76.34, 76.65–76.76, 89, 122, 324/456, 452, 500, 718; 73/799, 40, 73/49.3, 763, 863.33, 863.31, 170.29
See application file for complete search history.

(56) References Cited

U.S. PATENT DOCUMENTS

| | | | |
|---|---|---|---|
| 6,009,744 A | 1/2000 | Kovalchick et al. | |
| 6,694,268 B2 * | 2/2004 | Maruyama | G01M 3/40 324/557 |
| 9,759,687 B2 * | 9/2017 | Langois | G01M 3/40 |

FOREIGN PATENT DOCUMENTS

| | | |
|---|---|---|
| DE | 3915797 A1 | 11/1989 |
| DE | 102013014473 A1 | 3/2015 |
| EP | 0377208 A2 | 7/1990 |
| EP | 1965207 A1 | 9/2008 |
| JP | S64-46622 A | 2/1989 |

* cited by examiner

METHOD AND DEVICE FOR TESTING TEST OBJECTS FOR THE PRESENCE OF DAMAGE

CROSS-REFERENCE TO RELATED APPLICATIONS

This application is a 371 of PCT/EP 2016/075390 filed Oct. 21, 2016, which in turn claims the priority of DE 10 2015 118 287.4 filed Oct. 27, 2015, the priority of both applications is hereby claimed and both applications are incorporated herein by reference.

BACKGROUND OF THE INVENTION

The invention relates to a method and a device for testing consistent test objects for the presence of holes or cracks in a bottom surface, wherein each test object is bounded off by the bottom surface, an opening situated opposite the bottom surface, and a lateral surface extending between the opening and the bottom surface.

Typical test objects are for example plastic closure caps which are used to seal containers so as to be air-tight. Such closure caps may have a guarantee strip in the region of the opening edge, the so-called freshness seal, which is detached from the closure cap when opened. In order to facilitate this detaching, the guarantee strip is connected to the closure cap only by thin webs. The guarantee strip can be produced directly during the injection molding process of the closure cap. Another possibility is to make slits in the closure cap which are evenly distributed about the circumference, at slight distance from the opening edge. Moreover, closure caps are known with several flaps secured by webs to their opening edge, which can be brought to bear against the inside of the closure cap when screwed on. Such closure caps owing to the manufacturing process have openings between the guarantee strip or the'flaps and the lateral surface.

Plastic closure caps are usually produced as injection molded parts. During manufacture, leaky areas known as microholes or microcracks may occur in the bottom surface near the injection point. However holes and cracks must be avoided in the closure cap of a container, in order to prevent an unwanted escaping of the contents from the container closed with the closure cap or an unwanted entry of gases or liquids into the container.

Hence there is a need to automatically identify and sort out test objects, especially plastic closure caps, with such defects.

JP S64-046 622 A discloses a method for testing containers for tightness, in which the containers are transported continuously by means of a conveying mechanism in a transport plane, and by means of a high-voltage source a test voltage is applied between a stationary concentration electrode situated above the transport plane and a stationary side electrode situated in the transport plane when the container to be tested is found between the electrodes. A leak in the container is identified if a breakdown between the electrodes on account of the changing fill level in the container is identified by a current measuring device.

DE 32 13 100 A1 discloses a method of finding and sorting out defective ceramic objects in which the flaws are determined by electrostatic charging. The ceramic objects are moved continuously through a test station where they are subjected to consecutive high-voltage discharges, so that basically all areas of the ceramic objects are covered by the high-voltage discharges. The electrodes are arranged underneath the trajectory of the ceramic objects to be tested and correspond in their shape to the shape of the ceramic objects. Sensors are provided along the trajectory, which detect the ceramic objects to be tested and control the successive discharges of the electrodes according to a predetermined program. In this way, the objects can be fully tested during the movement and defects in the parts become noticeable in a charge pattern, which is detected by receiving electrodes. Fault signals activate a sorting mechanism, which removes the part found to be defective from the transport mechanism.

An electrode arrangement is known from DE 31 36 538 C2 comprising two electrodes for testing test objects for the presence of holes or cracks, wherein the two electrodes are polarized opposite to each other. One of the two electrodes stands in contact with the test object to be tested and the other electrode is partially adapted to the outer contour of the test object, which is moved past the electrodes by means of a conveyor along a transport path. The voltage applied to the electrodes generates a corona discharge current between the electrodes if the test object has no leak, and a spark discharge current between the electrodes if the test object has a leak, i.e. a microhole or crack.

Furthermore, from DE 10 2013 014 473 A1 there is known a device for testing plastic closure caps for the presence of microholes or microcracks, in which an electrode is designed as a finger of a star wheel, which is inserted into the closure cap as far as the bottom. A counter electrode is placed stationary on the other side of the bottom underneath a transporting mechanism for the closure caps, which has parallel transport belts running in the same direction. The closure caps when moving through the testing mechanism must not become damaged by the star wheel. A typical risk of damage consists in that the inserted finger does not dip into the closure cap, but instead strikes the opening edge. In order to avoid such damage, the closure caps are usually moved under the star wheel jammed seamlessly against one another, so that one finger after another can reach into the abutting closure caps without destruction. The build-up of the closure caps is accomplished in that the closure caps move more slowly in the jamming area in front of the star wheel than the transport mechanism. This can be achieved, for example, by regulating the speed of rotation of the star wheel relative to the speed of advancement of the transport belts.

However, the jamming together of the closure caps needed for their damage-free testing has several drawbacks:

- Because of the relative velocity between the transport belts of the transport unit and the closure caps, friction occurs, which can result in damaging of the closure caps, for example, an imprinted image placed on the top side of the closure cap.
- The build-up of the closure caps must have a certain minimum length so that under no circumstances can there occur a gap underneath the pin wheel. The minimum length requires a certain structural height of the testing mechanism, which may be a disadvantage when integrating it into the manufacturing facility.
- Insofar as closure caps with a guarantee strip or flaps are to be tested, the testing mechanism often has a so-called slitter for making the guarantee strip or a folder for making the flaps in front of it. For cost and space reasons, the testing mechanism and the upstream slitter or folder preferably have a common transport mechanism for the closure caps. The back-up of the closure caps needed for the testing mechanism however must in no case extend as far as the upstream slitter or folder, since these devices might become damaged in this way.

BRIEF SUMMARY OF THE PRESENT INVENTION

An object of the present invention is to create a method and device for testing consistent test objects for the presence of holes or cracks, which works without a back-up and friction between the test objects and the transport mechanism.

The object is met by a method and apparatus in which the electrodes do not come into contact mechanically with the test objects and the position of the test objects on the transport mechanism does not change.

According to an embodiment of the invention, an electrode arrangement is provided which comprises a stationary upper electrode situated above a transport plane and a stationary lower electrode situated beneath the transport plane, as well as a discharge path between the upper and lower electrode. The test objects are transported along a transport path lying in the transport plane between the upper and the lower electrode, without touching the electrodes. The transport of the test objects in the transport plane occurs in particular with a transport mechanism comprising two parallel transport belts running in the same direction, as is known for example from DE 10 2013 014 473 A1.

In order to detect microholes and cracks in the test objects, the size of the test voltage is controlled so that it is greater than or equal to the breakdown voltage between the electrodes in air, but smaller than the breakdown voltage through a flawless test object without holes or cracks between the electrodes. By breakdown voltage is meant here that voltage which is needed to let current flow through an insulator.

Thanks to the noncontact, nonjammed transport, gaps occur between the test objects on the transport path. In order to prevent breakdowns between the electrodes in these gaps, the test voltage between the electrodes is controlled temporally and synchronized with the movement of the test objects so that the test voltage between the electrodes is only present when one of the test objects is present between the upper and lower electrode. A typical test voltage between the electrodes lies on the order of around 30 kV. In order to safely control such large test voltages, the test voltage is generated by a first controlled voltage source and a second voltage source, the two voltage sources being connected in electrical series. The sum of the voltages generated by the two voltage sources is applied as test voltage to the electrodes.

The voltage of the first, controlled voltage source is only generated when one of the test objects is found between the electrodes, while the voltage of the second voltage source is generated continuously during the testing. The size of the continuously generated voltage is preferably just below the breakdown voltage between the electrodes in air. The size of the voltage generated by the first, controlled voltage source which is needed to achieve the test voltage is therefore relatively small, so that the loading of the switching elements for switching the first controllable voltage source on and off is significantly reduced.

In this way, a significantly improved reliability of the device for carrying out the test method of the invention is achieved, given the many control processes over its useful life.

The determination of whether a hole or crack is present in the test object includes recognizing a breakdown on the discharge path between the electrodes. If a hole or crack occurs in the bottom surface of the object, the insulating action of the test object is lacking in the region of the hole or crack. Since the test voltage is greater than or equal to the breakdown voltage between the electrodes in air, a breakdown occurs on the discharge path between the electrodes, manifested as a current flowing between the electrodes.

In order to assure the noncontact transport of the test objects along the transport path, the distance between the upper and lower electrode is adjusted as a function of the largest dimension of the particular test objects to be tested perpendicular to the transport plane. The transport plane is defined by the supporting surface of the transport mechanism, especially the preferably parallel transport belts running in the same direction. Closure caps are typically transported with the opening facing upward, so that the size of the closure caps corresponds to the largest dimension perpendicular to the transport plane. Normally the size of the closure caps is between 8 mm and 20 mm. The distance between the lower and upper electrode should be chosen only slightly larger, e.g. by no more than 2 mm, than the size of the closure caps, in order to avoid needlessly high test voltages.

For the control of the test voltage between the electrodes, it is advantageous when the first voltage source generates a time-variable voltage. The voltage source can be designed as an alternating voltage source, generating a voltage varying periodically over time. For example, one may consider an alternating voltage source with 100 kHz. However, the voltage source can also be controlled so that only one or more voltage pulse(s) is/are generated by the first voltage source when one of the test objects is located between the electrodes.

In an embodiment of the invention, the first voltage source for generating a time-variable voltage comprises a transformer with a secondary side and a primary side, while the control of the first voltage source occurs via the primary side. The control can occur on the primary side with the customary industrial power supply voltage of 24 Volts, so that the many switching events will hardly burden the voltage source. In this way, a high reliability of the testing device is achieved. In addition, the power uptake is slight, because the test voltage per test object is only provided for a short time.

For a reliable recognition of a breakdown between the two electrodes, it is advantageous when the second voltage source generates a d.c. voltage and when the breakdown recognition occurs at the second voltage source.

In order to reduce the expense for the control of the first voltage source, the first and second voltage source are connected in electrical series preferably by connection to a common ground point.

Insofar as the test objects owing to the manufacturing process have openings, such as plastic closure caps with guarantee strip or flaps, it must be prevented that a breakdown occurs on an unintended discharge path through these openings. In such a case, the closure cap would be identified as defective and sorted out. However the removal of possibly flawless closure caps is undesirable for economic reasons.

In order to prevent breakdowns on an unintended discharge path, an electrode arrangement is preferably provided having rod-shaped electrodes which are aligned with each other. The first voltage source is controlled during the testing of test objects with a bottom surface having a center point in such a way that a voltage of the first voltage source is only generated when the center point is in alignment or in a determined, preferably concentric region around the alignment, the region being significantly smaller than the bottom surface. In this way, any manufacturing-related openings between the opening edge of the closure cap and the guarantee strip or the flaps are as far away from the rod-shaped electrodes as possible, so that breakdowns on an unintended discharge path are for the most part prevented.

Further measures to prevent a breakdown along an unintended discharge path consist in influencing the course of the intended discharge path by specific ionization of the air and/or by a magnetic field and/or electric field:

The specific, spatially limited ionization of the air along the intended discharge path at the shortest distance between the electrodes can be accomplished for example with the aid of focused and spatially concentrated optical radiation, preferably in the ultraviolet range. Moreover, a specific ionization of the air can be done with the aid of switched lasers or radioactive sources. In addition, the propagation of the ionization can be influenced by a directed air flow.

Magnetic fields can be generated by both permanent magnets and also electromagnets, whose field lines run parallel to the intended discharge path.

Finally, the course of the discharge path can be influenced by electric fields. For this, the rod-shaped electrodes can taper to a tip with a radius of less than 1 mm, in particular, on their sides facing the test object.

For the position-dependent control of the first voltage source, the position of the test object on the transport path between the upper and lower electrode is detected preferably with the aid of at least one sensor. As sensors, one may consider for example light barriers, light scanners, or other sensors, such as tactile sensors.

In order to reduce the number of rejects during the manufacture of the test objects depending on the test result for the test objects, it is provided in one embodiment of the method according to the invention that the test objects during the transport along the transport path additionally move through an optical testing device, which is designed to read information molded into the test objects. For injection-molded closure caps, this information might be a cavity number allowing a tracing back to the mold nest of the injection molding die from which the defective test object comes. Since the testing of the test objects for microholes or microcracks occurs on the same transport path as the optical testing, the test result as to the presence of microholes or microcracks in the closure caps can be correlated with the cavity number and thus allow an evaluation of defect frequency in terms of mold nest. In this way, suitable measures can be adopted early on during the manufacturing of the closure caps, in order to reduce the defect frequency. For example, upon finding a cluster of defective closure caps from a particular mold nest, the feedback of the test results can enable the elimination of a mold nest and thereby reduce the production of rejects.

BRIEF DESCRIPTION OF THE DRAWINGS

The invention shall be explained more closely hereinafter with the aid of the figures. There are shown.

DETAILED DESCRIPTION OF THE PREFERRED EMBODIMENTS

Figure 1:
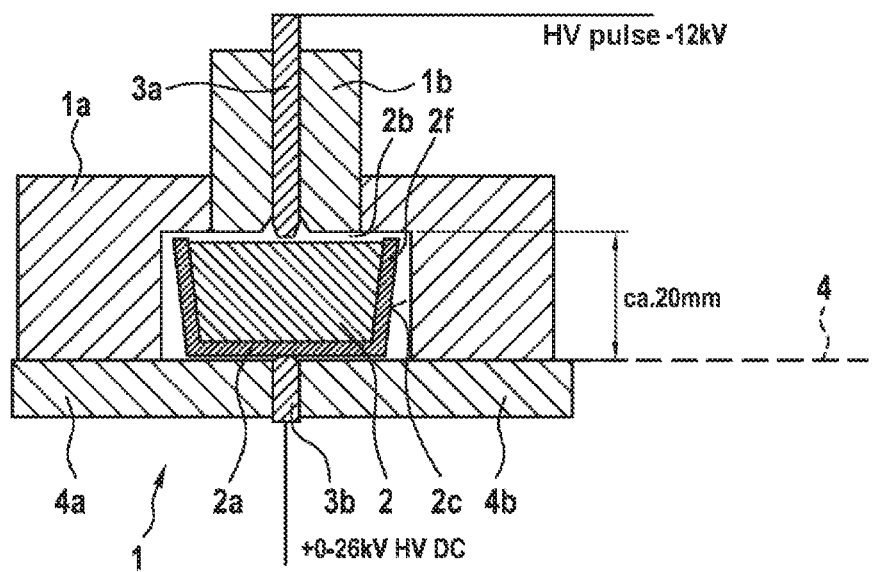
FIG. 1 a schematic representation of an electrode arrangement as well as a transport mechanism of a device to carry out the method according to the invention, FIG. 2 a schematic representation of a first and second voltage source for generating a test voltage in a device to carry out the method according to the invention, FIG. 3 a schematic representation of various closure caps with guarantee strip or flaps at the upper opening edge, FIG. 4 a schematic representation of a breakdown along an unintended discharge path, FIG. 5 a schematic representation of an electrode arrangement with an ionization device for influencing the discharge path, and FIG. 6 a schematic representation of a magnetic field for influencing a discharge path according to an embodiment of the invention.

FIG. 1 shows schematically a portion of a device (1) for testing consistent test objects (2) for the presence of holes or cracks in a bottom surface (2a), wherein each test object (2) is bounded off by the bottom surface (2a), an opening (2b) situated opposite the bottom surface (2a), and a lateral surface (2c) extending between the opening (2b) and the bottom surface (2a). The test objects (2) in particular are injection-molded plastic closure caps for the sealing of containers.

Figure 3A:
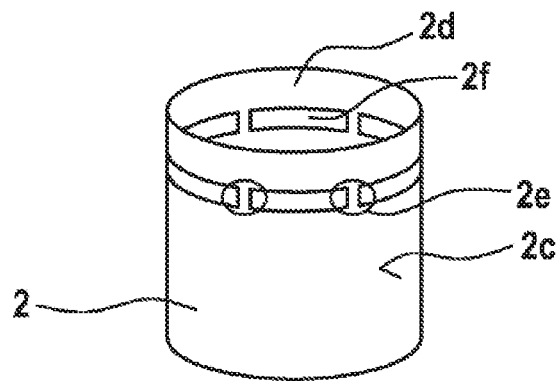
Figure 3B:
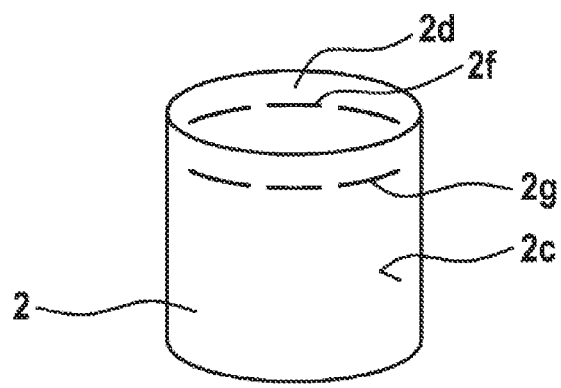

FIGS. 3a, 3b show closure caps (2) with a guarantee strip (2d). The guarantee strip (2d) in the closure cap (2) of FIG. 3a is secured by narrow webs (2e) to the edge (2f) bordering on the opening (2b). In the closure cap (2) of FIG. 3b, slits (2g) along the periphery of the edge (2f) separate the guarantee strip (2d) from the lateral surface (2c).

Figure 3C:
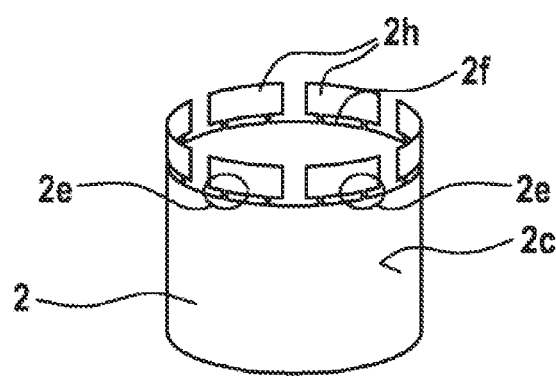

The closure cap of FIG. 3c has several flaps (2h) along the edge (2f) at the opening (2b), which are elastically connected by webs (2e) to the edge (2f) along the opening (2b).

The guarantee strip (2d) is to be loosened from the closure cap upon opening. The flaps upon opening of the closure cap move from the inside of the closure cap to the outside.

An electrode arrangement (3) of the device (1) comprises a stationary upper rod-shaped electrode (3a) situated above a transport plane (4) and a stationary lower rod-shaped electrode (3b) situated beneath the transport plane (4), as well as a discharge path (3c). Between the upper electrode (3a) and the lower electrode (3b) a test voltage (10) is temporarily present, which is generated by a first and a second voltage source (5, 6).

Figure 2:
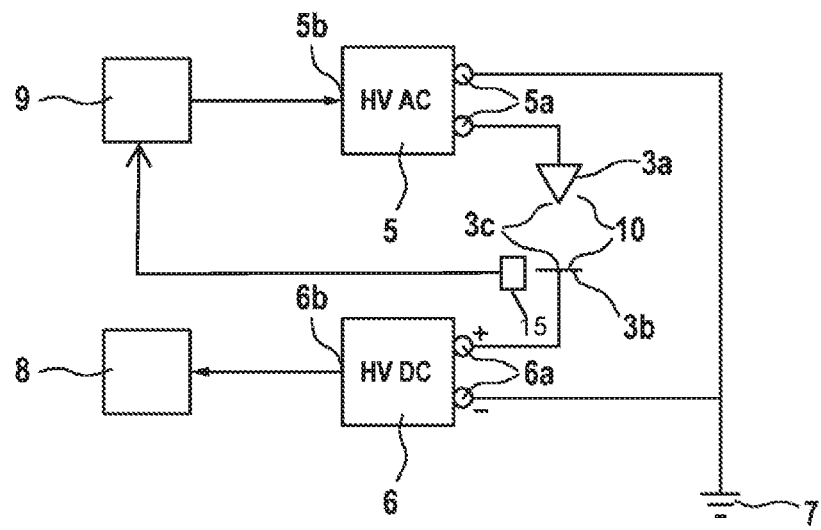

The first, controlled voltage source (5) in the sample embodiment depicted in FIG. 2 is an alternating voltage source, which generates a time-variable voltage with an amplitude of 12 kV on the terminals (5a). The alternating voltage source comprises a transformer (not shown) at whose primary side an input alternating voltage of 24 Volts is temporarily present, being switched by a control unit (9), and which is transformed by the transformer to the terminal voltage thanks to its transformation ratio.

The second voltage source (6) in the sample embodiment depicted in FIG. 2 is a d.c. voltage source, which generates a d.c. voltage of 26 kV on the terminals (6a). The d.c. voltage source likewise comprises a transformer, which transforms the input alternating voltage into the rectified terminal voltage of 26 kV.

As is further evident from FIG. 2, the d.c. voltage source (6) and the alternating voltage source (5) are each connected together across a ground point (7) which is common to their two terminals (5a, 6a). The electrodes (3a, 3b) are each connected to the other terminals (5a, 6a) of the alternating voltage source (5) and the d.c. voltage source (6). Thanks to this circuit arrangement, a series connection of the d.c. voltage source (6) to the alternating voltage source (5) across the discharge path (3c) is produced.

The d.c. voltage source (6) is connected by an output (6b) to an evaluation device (8) for recognizing a breakdown on the discharge path (3c) between the electrodes (3a, 3b).

The alternating voltage source (5) has a control input (5b), which is connected to the control unit (9). The control unit (9) switches the alternating voltage source (5) via the control input (5b) such that an alternating voltage is only generated on the terminals (5a) when one of the test objects (2) is located between the upper electrode (3a) and the lower electrode (3b), as is shown schematically in FIG. 1. At the same time, the control unit (9) ensures that the voltage of the d.c. voltage source (6) is continuously present at the terminals (6a) during the testing of test objects (2), while the sum of the voltage generated by the alternating voltage source (5) and the d.c. voltage source (6) is applied as test voltage (10) between the electrodes (3a, 3b), thanks to the series connection.

Moreover, the control unit (9) controls the alternating voltage source (5) and the d.c. voltage source (6) so that the size of the test voltage (10) is greater than the breakdown voltage between the electrodes (3a, 3b) in air, i.e., in the absence of a test object (2) between the electrodes (3a, 3b).

At the same time, the control unit (9) limits the test voltage (10) to a value which is smaller than the breakdown voltage between the electrodes (3a, 3b) through a flawless test object (2) without holes or cracks in the bottom surface (2a).

This controlling of the test voltage ensures that a breakdown only occurs on the discharge path (3c) when the test object (2) has a hole or crack in the bottom surface (2a). In this case, the discharge path (3c) extends between the upper electrode (3a) through the hole or crack to the lower electrode (3b). Since the test voltage is larger than the breakdown voltage in air, a breakdown will occur, i.e., an electric current will flow across the discharge path (3c).

In order to transport the test objects (2) along a transport path lying in the transport plane (4) and extending perpendicular to the plane of the drawing in FIG. 1, the device (1) preferably has two parallel transport belts (4a, 4b) running in the same direction. The two transport belts (4a, 4b) are arranged at a distance from one another so that the lower electrode (3b) extends as far as the surface of the transport plane (4) which is formed by the surface of the transport belts (4a, 4b) in the upper branch.

On a supporting frame (1a) of the device (1) a height-adjustable holder (1b) is arranged, which holds the upper electrode (3a) flush with the lower electrode (3b). The holder (1b) consists of an insulating material, in which the electrode is embedded. With the help of the height-adjustable holder (1b) for the upper electrode (3a), the distance between the upper and lower electrode (3a, 3b) can be adjusted in dependence on the largest dimension of the test objects (2) to be tested—here, the size of the closure caps—perpendicular to the transport plane (4). The distance is adjusted to be as small as possible, so that the upper electrode (3a) almost collides with the upper edge (2f) of the test object (2). The distance of the upper electrode to the edge (2f) of the test object in the vertical direction to the transport plane (4) should be at most 2 mm.

In the sample embodiment shown, the closure caps have a circular-cylindrical bottom surface with a center point. In such test objects (2), the alternating voltage source (5) is actuated by the control unit (9) so that a voltage is only applied on the terminals (5a) when the center point is in alignment with the two electrodes (3a, 3b) or in a small concentric determined region around the alignment. Thanks to the centering of the test objects (2) with respect to the electrodes (3a, 3b), a breakdown along an unintended discharge path can be avoided. The openings between the guarantee strip (2d) or the flaps (2b) of a closure cap, which are not to be tested, are situated thanks to a centering at the greatest possible distance between the electrode tips, so that with proper height adjustment of the upper electrode (3a) breakdowns will occur almost exclusively through any microholes or microcracks which are to be detected, especially since these are usually located in the region of the injection point, i.e., at the center point of the bottom surface.

Figure 4:
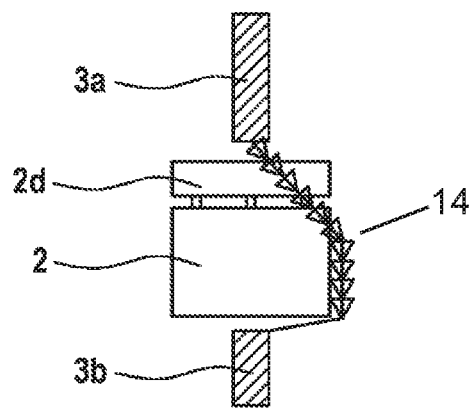
Figure 5:
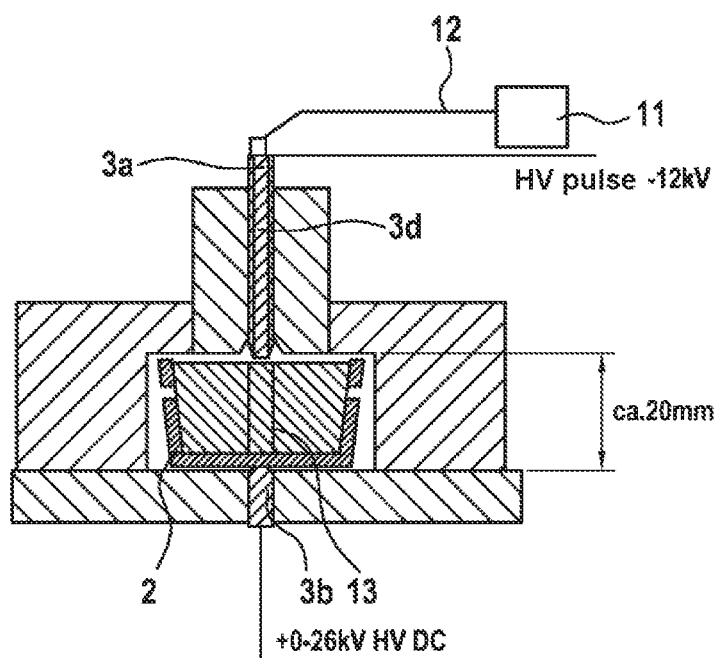

FIG. 4 illustrates a breakdown 14 along an unintended discharge path for a closure cap corresponding to FIG. 3a-3c. In order to prevent the unintended breakdown 14, there is the additional option shown in FIG. 5 for the device to have a radiation source (11) suitable for the ionization of the air along the discharge path (3c), wherein the UV radiation generated by the radiation source (11) is coupled via a waveguide (12) into a central borehole (3d) passing through the upper electrode (3a), from which the radiation emerges at the lower end thereof in the direction of the lower electrode (3b). The radiation creates an ionized region (13) between the electrodes (3a, 3b).

Figure 6:
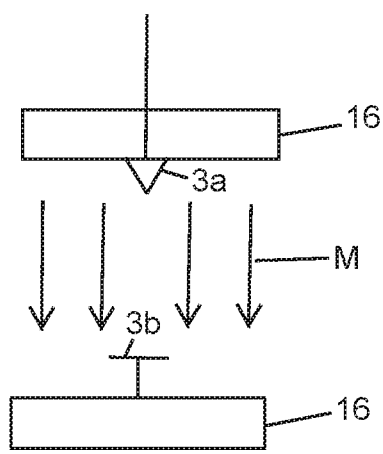

FIG. 6 shows an alternative or additional embodiment in which a magnetic 16 (shown schematically) generates magnetic field lines M that run parallel to an intended discharge path to aid in preventing a breakdown along an unintended discharge path. The magnet 16 may be a permanent magnet or an electromagnet. As a further measure, the rod-shaped electrodes (3a, 3b) may be tapered (see FIG. 1) to a tip with a radius of <1 mm on the sides facing the test object to generate an electrical field to influence the course of the discharge Path.

In order to detect the position of the test objects (2) on the transport path between the electrodes (3a, 3b), the control system (9) is connected to at least one sensor 15 (shown schematically in FIG. 1), such as a light barrier.

If the sensors detect that one of the test objects is situated centrally between the electrodes (3a, 3b), as shown in FIG. 1, the alternating voltage source (5) generates the alternating voltage on the terminals (5a) for the period of the testing, this being added with the d.c. voltage on the terminals (6a) of the d.c. voltage source (6) to the test voltage (10). During the transport of the test objects (2) along the transport path, only a slight deviation of the position of the test objects transversely to the course of the transport path is allowed. Otherwise, a central orienting of the test objects (2) to the upper and lower electrode (3a, 3b) with the aid of the sensors is not possible. As a guide, a positional tolerance of at most +/−2 mm, preferably +/−1 mm transversely to the transport path can be tolerated. The observance of the positional tolerance is ensured by precise placement of the test objects on the transport system.

The evaluation device (8) recognizes a breakdown on the discharge path (3c) between the upper and the lower electrode (3a, 3b) by the occurrence of a flow of current in the d.c. voltage source (6). If a defective test object is recognized in this way, it is automatically sorted out.

| No. | Reference |
|---|---|
| 1 | device |
| 1a | supporting frame |
| 1b | holder |
| 2 | test object |
| 2a | bottom surface |
| 2b | opening |
| 2c | lateral surface |
| 2d | guarantee strip |
| 2e | webs |
| 2f | edge |

-continued

| No. | Reference |
|---|---|
| 2g | slits |
| 2h | flap |
| 3 | electrode arrangement |
| 3a | upper electrode |
| 3b | lower electrode |
| 3c | discharge path |
| 3d | central borehole |
| 4 | transport plane |
| 4a, b | transport belts |
| 5 | first voltage source |
| 5a | terminals |
| 5b | control input |
| 6 | second voltage source |
| 6a | terminals |
| 6b | output |
| 7 | ground point |
| 8 | evaluation |
| 9 | control system |
| 10 | test voltage |
| 11 | UV radiation source |
| 12 | waveguide |
| 13 | ionized region |

The invention claimed is:

1. A method for testing consistent test objects for the presence of holes or cracks in a bottom surface, wherein each test object includes the bottom surface, an opening situated opposite the bottom surface, and a lateral surface extending between the opening and the bottom surface, the method comprising the steps of:
providing an electrode arrangement with two electrodes comprising a stationary upper electrode disposed above a transport plane and a stationary lower electrode disposed beneath the transport plane, a discharge path being defined between the upper electrode and the lower electrode,
connecting a first voltage source to one of the two electrodes and connecting a second voltage source to the other of the two electrodes, the first voltage source and the second voltage source being connected in electrical series across the discharge path,
transporting each of the test objects along a transport path lying in the transport plane, which extends between the upper electrode and the lower electrode,
controlling the first voltage source and the second voltage source such that a voltage of the first voltage source is generated only when one of the test objects is positioned between the upper electrode and the lower electrode, and a voltage of the second voltage source is generated continuously during the testing of the test objects, a sum of the voltages generated by the first voltage source and the second voltage source is applied as a test voltage to the two electrodes,
controlling a size of the test voltage so that it is greater than or equal to a breakdown voltage between the two electrodes in air and smaller than a breakdown voltage between the two electrodes through a flawless test object without holes or cracks, and
determining whether holes or cracks are present in a test object disposed between the two electrodes by recognizing a breakdown between the electrodes.

2. The method as claimed in claim 1, wherein the each of the test objects is transported along the transport path between the upper electrode and the lower electrode without touching the upper electrode and the lower electrode.

3. The method as claimed in claim 1, wherein a distance between the two electrodes is adjusted as a function of a largest dimension of the test objects perpendicular to the transport plane.

4. The method as claimed in claim 1, wherein the first voltage source generates a time-variable voltage.

5. The method as claimed in claim 4, wherein the first voltage source comprises a transformer with a secondary side and a primary side, and control of the first voltage source occurs by switching on and off an input voltage applied at the primary side.

6. The method as claimed in claim 1, wherein the second voltage source generates a time-constant voltage.

7. The method as claimed in claim 1, wherein the first voltage source and the second voltage source are connected in electrical series by connection to a common ground point.

8. The method as claimed in claim 1, wherein the upper electrode and the lower electrode are rod-shaped electrodes which are aligned with each other.

9. The method as claimed in claim 8, wherein the first voltage source is controlled during the testing of test objects in such a way that a voltage of the first voltage source is generated when a center point of the bottom surface of one of the test objects is in alignment with the rod-shaped electrodes or in a determined region around the alignment, the determined region being smaller than the bottom surface.

10. The method as claimed in claim 1, wherein the position of the each test object between the two electrodes on the transport path is detected with a sensor.

11. The method as claimed in claim 1, wherein a size of the voltage generated by the first voltage source is at most 50% of the size of the voltage generated by the second voltage source.

12. The method as claimed in claim 1, wherein a breakdown is recognized when a current flows between the upper and lower electrode.

13. The method as claimed in claim 1, wherein a breakdown is recognized when a size of the voltage generated by the second voltage source decreases temporarily.

14. The method as claimed in claim 1, wherein a course of the discharge path is influenced by specific ionization of the air between the two electrodes.

15. The method as claimed in claim 1, wherein a course of the discharge path is influenced by at least one magnetic field.

16. The method as claimed in claim 1, wherein the test objects are plastic injection-molded test objects.

17. The method as claimed in claim 16, further comprising the step of moving the test objects during the transport along the transport path through an optical testing device designed to read information molded into the test objects.

18. A device for testing consistent test objects for the presence of holes or cracks in a bottom surface, wherein each test object includes the bottom surface, an opening situated opposite the bottom surface, and a lateral surface extending between the opening and the bottom surface, the device comprising:
an electrode arrangement with two electrodes including a stationary upper electrode disposed above a transport plane and a stationary lower electrode disposed beneath the transport plane, a discharge path being defined between the upper electrode and the lower electrode,
a first voltage source connected to one of the two electrodes and a second voltage source connected to the other of the two electrodes, the first voltage source and the second voltage source being connected in electrical series across the discharge path, a transport mechanism transporting each of the test objects along a transport path lying in the transport plane, which extends between the upper electrode and the lower electrode, a control system controlling the first voltage source and the second voltage source such that a voltage of the first voltage source is generated only when one of the test objects is positioned between the upper electrode and the lower electrode, a voltage of the second voltage source is generated continuously during the testing of the test objects, a sum of the voltages generated by the first voltage source and the second voltage source is applied as a test voltage between the electrodes, and the size of the test voltage being greater than or equal to a breakdown voltage between the two electrodes in air and smaller than a breakdown voltage between the two electrodes through a flawless test object without holes or cracks between the electrodes, and an evaluation device for recognizing a breakdown on the discharge path between the two electrodes.

19. The device as claimed in claim 18, wherein a distance between the upper electrode and the lower electrode is adjustable.

20. The device as claimed in claim 18, wherein the first voltage source generates a time-variable voltage.

21. The device as claimed in claim 20, wherein the first voltage source comprises a transformer with a secondary side and a primary side, an input voltage controlled by the control system is temporarily applied to the primary side, and a ratio between the voltage generated on the secondary side to the input voltage is greater than 100:1.

22. The device as claimed in claim 18, wherein the second voltage source is a d.c. voltage source.

23. The device as claimed in claim 18, wherein the two electrodes are rod-shaped electrodes which are aligned with each other.

24. The device as claimed in claim 18, further comprising a sensor connected to the control system and designed to detect the position of one of the test objects on the transport path between the electrodes.

25. The device as claimed in claim 18 where in the evaluation device includes a current measuring device to measure a flow of current between the upper and lower electrode.

26. The device as claimed in claim 18, wherein the evaluation device includes a voltage measuring device to measure the size of the voltage generated by the second voltage source.

27. The device as claimed in claim 18, further comprising a radiation source suitable for ionization of air, the radiation source being arranged such that the air is ionized along the discharge path.

28. The device as claimed in claim 18, further comprising a magnet arranged in the vicinity of the discharge path, wherein the field lines of the magnetic field run parallel to the discharge path.

29. The device as claimed in claim 18, further comprising an optical testing device arranged along the transport path and designed to read information molded into the test objects.

* * * * *